United States Patent [19]
Kanzaki et al.

[11] 3,948,726
[45] Apr. 6, 1976

[54] PRODUCTION OF CEPHALOSPORIN C

[75] Inventors: Toshihiko Kanzaki, Hyogo; Yukio Fujisawa; Haruo Suide, both of Osaka, all of Japan

[73] Assignee: Takeda Chemical Industries, Ltd., Osaka, Japan

[22] Filed: Sept. 30, 1974

[21] Appl. No.: 510,862

[30] Foreign Application Priority Data
Oct. 1, 1973  Japan.............................. 48-110723

[52] U.S. Cl............................................. 195/36 C
[51] Int. Cl.².......................................... C12D 9/04
[58] Field of Search ....................... 195/36 R, 36 C

[56] References Cited
UNITED STATES PATENTS

| | | | |
|---|---|---|---|
| 3,776,815 | 12/1973 | Treichler et al. | 195/36 R |
| 3,816,257 | 6/1974 | Yamano et al. | 195/36 R |

*Primary Examiner*—Alvin E. Tanenholtz
*Attorney, Agent, or Firm*—Wenderoth, Lind & Ponack

[57] ABSTRACT

A new process for the production of Cephalosporin C (CPC) in which a polyene-antibiotics-resistant mold of the genus Cephalosporium is employed and an increased yield is attained.

CPC is an antibiotic and also useful as a starting material for the synthesis of Cephalosporin-group antibiotics.

5 Claims, No Drawings

PRODUCTION OF CEPHALOSPORIN C

This invention relates to a method for the production of cephalosporin C. More particularly, this invention relates to a method for the production of cephalosporin C, which comprises cultivating a cephalosporin C-producing and polyene-antibiotics-resistant mold belonging to the genus Cephalosporium in a culture medium, thereby letting said mold accumlate an increased amount of cephalosporin C in said medium, and then recovering thus accumulated product therefrom.

Cephalosporin C (hereafter sometimes referred to as CPC) is an antibiotic per se (H.W. Florey: Ann. Int. Med., 43,480 (1955) and is also useful as a starting material for the synthesis of cephalosporin-group antibiotics (R.R. Chauvette et al. J. Am. Chem. Soc., 84,3401(1962)). It is known that cephalosporin C can be produced by growing certain microorganisms such as *Cephalosporium acremonium*, *Cephalosporium polyaleurum*, *Emericellopsis glabra*, *Emericellopsis microspora*, etc. However, the methods using these microorganisms have the disadvantage that the CPC-producing abilities of the strains are so low that the costs of production of CPC are of necessity considerable.

Under the circumstances we made an exploratory study to develop a method by which CPC could be produced profitably on a commercial scale. The study led us to the fact that among polyene-antibiotics-resistant molds of CPC-producers belonging to the genus Cephalosporium, there was found a mutant, in a higher frequency than among other types of mutants, which is capable of accumulating CPC in a surprisingly high concentration, i.e., 9,000 $\mu$g/ml. and preferably 10,000 $\mu$g/ml. or more of CPC. The finding was followed by further studies which have culminated in the present invention.

Thus, the main object of this invention is to provide a new method for the increased production of CPC.

Another object of this invention is to provide a process for the selection of mold which can accumulate an increased amount of CPC.

Further objects will be illustrated in the following descriptions.

The microorganisms which are to be employed in this invention are CPC-producing and polyene-antibiotics-resistant molds of the genus Cephalosporium, and molds belonging to the species *Cephalosporium acremonium* or *Cephalosporium polyaleurum* may be mentioned as preferred examples.

Polyene-antibiotics are antibiotic substances possessing one or more of multiple-membered lactones having four to seven conjugated double bonds in their molecule, and include kabicidin (Japanese Pat. No. 247306), nystatin [Proc. Soc. Exper. Exp. Biol. Med., 76, 93(1951)], trichomycin [Antibiotiki, 9, 291 (1964)], etc. as typical examples. The term 'polyene-antibiotics-resistant mold' as used herein means any mold which is induced from a parent microorganism (CPC-producing mold of the genus Cephalosporium) and has an increased resistance to polyene-antibiotics of not less than 20 percent over the corresponding resistance of the parent, that is to say, a mutant such that the minimal inhibitory concentration (MIC) of polyene-antibiotics against it is not less than about 120 percent of the minimal inhibitory concentration against the parent microorganisms using agar dilution method under the following test conditions:

The basic medium for the test: peptone 1 %, meat extract 0.5 %, NaCl 0.25 %, agar 2.0 % (pH 7.0). Cultivation: 28°C, 4 days.

It has been reported that polyene antibiotics exert antifungal actions by combining themselves with the sterols of fungal cell membranes [Annual Review of Pharmacology, 10, 119(1970)]. Therefore, it is expected that a microorganism resistant to a given polyene antibiotic has cross-resistances to other polyene antibiotics, that is to say, when a strain is resistant to any one of polyene-group antibiotics, it is also resistant to other members of the polyene group.

Induction of a polyene-antibiotics-resistant mold can be performed in a conventional manner. Thus, in one of the methods thus far known, the microorganism to which one wishes to impart resistance is grown on a fluid or agar medium containing the particular antibiotic in a concentration approximating its minimal inhibitory concentration, and the concentration of the antibiotic in the medium is serially increased to adapt the microorganism until the desired resistant mold is obtained. In another method, the microbial cells are first treated with a conventional mutagen, e.g. ultraviolet-ray, X-rays or NTG(N-methyl-N'-nitro-N-nitrsoguanidine) and, then, propagated on a fluid or agar medium containing the polyene antibiotic in a concentration in excess of its minimal inhibitory concentration, and the microbial growth formed is harvested as the resistant mold.

These methods may not only be practiced in repetition but may also be carried out in combination with other breeding methods of microorganisms. By such procedures, still improved results can be achieved.

The following are some typical examples of polyene-antibiotics-resistant molds of CPC-producers belonging to the genus Cephalosporium. *Cephalosporium acremonium* K-121 (FERM-P No. 2285, ATCC-20427, IFO-9998) which has been induced from *C. acremonium* ATCC-14553; *Cephalosporium acremonium* N-75 (FERM-P No. 2286, ATCC-20428, IFO-9997) which has also been induced from *C. acremonium* ATCC-14553; *Cephalosporium polyaleurum* K-771 which has been induced from *C. polyaleurum* 199(ATCC-20359); *Cephalosporium polyaleurum* N-717 which is a mutant induced from *C. polyaleurum* Y-505(ATCC-20360), etc.

The numbers attached to the above microorganisms with the indications FERM-P, ATCC and IFO represent the deposit numbers at the Research Institute of Fermentation of the Agency of Industrial Science and Technology (FERM), Chiba, Japan; American Type Culture Collection (ATCC), Maryland, U.S.A.; and Institute for Fermentation, Osaka (IFO), Osaka, Japan, respectively.

Among the microorganisms mentioned above *Cephalosporium acremonium* K-121 and *Cephalosporium acremonium* N-75 are mutually similar and the most suitable molds for the purpose of the present invention. Their microbiological characteristics are as follows:

Colonies orbicular, dense, floccose, at first white, later very light rose-colored; vegetative hyphae hyaline, sparsely septate, branched. Conidiophores arises as side branches on aerial hyphae, erect, simple, nonseptate, 40–60 × 3 $\mu$. Conidia numerous, elliptical or oblong, straight or curved, nearly hyaline, 4 × 1–1.5 $\mu$.

The medium to be employed in the method of this invention may be one of the media used in the cultivation of conventional Cephalosporium strains.

Thus, as the assimilable carbon sources, there may be mentioned carbohydrates (e.g. glucose, sucrose, starch, soluble starch, waste molasses, etc.), n-paraffins, acetic acid, methanol, ethanol, glycerol, sorbitol, etc. As the digestible nitrogen sources, there may be mentioned, among others, inorganic nitrogen compounds (e.g. ammonium chloride, ammonium sulfate, ammonium nitrate, ammonium phosphate, potassium nitrate, etc.) and organic nitrogen compounds (e.g. urea, meat extract, peptone, soybean meal, cotton seed cake, peanut cake, dried yeast, corn steep liquor, yeast extract, casein, etc.). As metallic salts, the sulfates, hydrochlorides, nitrates, carbonates, phosphates, etc. of sodium, potassium, calcium, magnesium, manganese, zinc, iron, copper, etc. may be added, if necessary. Further, amino acids (e.g. methionine, cystine, cysteine, serine), thiosulfates, fatty acid esters, and such oils as lard oil, olive oil, etc., may also be incorporated, if necessary. As regards the conditions of cultivation, it is advantageous to grow the molds under aerated submerged conditions. The temperature is preferably within the range of 15° to 37°C and, for still better results, within the range of 18° to 35°C. The pH may lie within the range of 2 to 10 and, preferably, within the range of 4 to 9, while the cultivation time may range from 48 to 480 hours and, preferably, from 72 to 360 hours.

Since a predominance of CPC occurs in filtered broth, it is advantageous to centrifuge or filter the broth to remove the cells and purify CPC from the filtrate or supernatant. For example, the desired result can be achieved with advantage by using an ion exchange resin, activated carbon, nonionic copolymer, gel filtration, etc. in a suitable combination.

The following examples are further illustrative of the invention, it being of course to be understood that this invention is by no means limited thereto. Incidentally, the quantitative determination of CPC was performed by an enzymatic assay method using the cephalosporinase of *Aerobacter cloacae* IFO 12937 (deposited at the Institute for Fermentation, Osaka).

Thus, while CPC has an absorption maximum at 260 m$\mu$, this absorption is lost when cephalosporinase is permitted to act upon it. The determination of CPC was carried out by taking advantage of the difference.

In the following examples the relationship between part(s) by weight and part(s) by volume is that between gram(s) and milliliter(s).

EXAMPLE 1

A fermenter with 2,000 parts by volume in capacity is filled with 500 parts by volume of an inoculum medium made up of 3.0 % of sucrose, 1.5 % of meat extract, 0.5 % of corn steep liquor and 0.15 % of $CaCO_3$ which, after sterilization, is inoculated with *Cephalosporium acremonium* K-121 (FERM-P No. 2285)(The MIC of kabicidin against this strain is 7.0 $\mu$g/ml, while the MIC of the same antibiotic against the parent strain is 2.5 $\mu$g/ml). The inoculated fermenter is incubated at 28°C for 3 days. Meanwhile a stainless-steel tank fermenter with 50,000 parts by volume in capacity is charged with 30,000 parts by volume of a medium made up of 6 % of sucrose, 5 % of glucose, 3 % of peanut cake, 3 % of soybean meal, 1.0 % of DL-methionine and 0.15 % of $CaCO_3$. The medium is sterilized and cooled in the routine manner. This fermentation medium is aseptically inoculated with the inoculum culture prepared above and incubated at 28°C under sparging and agitation(aerated at 30,000 parts by volume/min and agitated at 250 r.p.m.). After a cultivation time of 190 hours, the fermentation broth is withdrawn and filtered to free it of solid matter.

The resultant filtrate (26,000 parts by volume) is assayed for CPC content. The titer of CPC found to be is 10,100 $\mu$g/ml.

The CPC is fractionally recovered in the following manner. The above filtrate (26,000 parts by volume) is passed down through a column of activated carbon (20,000 parts by volume) whereby the CPC is adsorbed on the carbon. The column is first washed well with water and then CPC is eluted with a 5 % aqueous solution of butanol containing 0.01 N NaOH, whereupon 33,000 parts by volume of CPC fractions are obtained. These CPC fractions are pooled and concentrated.

The concentrate is neutralized to pH 7.0 with NaOH and a sufficient amount of ethanol is added to the concentrate to give an ethanol concentration of 70 % (V/V). The procedure gives 182 parts by weight of crude crystals of CPC sodium dihydrate.

EXAMPLE 2

A fermenter with 2,000 parts by volume in capacity is filled with 500 parts by volume of an inoculum medium made up of 3.0 % of sucrose, 1.5 % of meat extract, 0.5 % of corn steep liquor and 0.15 % of $CaCO_3$ which, after sterilization, is inoculated with *Cephalosporium acremonium* N-75 (FERM -P No. 2286)(The MIC of nystatin against this strain is 6.0 $\mu$g/ml while the MIC of the same antibiotic against the parent strain is 1.7 $\mu$g/ml). The inoculated flask is incubated at 28°C for 3 days.

Meanwhile, a stainless-steel fermenter with 50,000 parts by volume in capacity is charged with 30,000 parts by volume of a fermentation medium made up of 6 % of sucrose, 5 % of glucose, 3.0 % of peanut cake, 3 % of soybean meal, 1.0 % of DL-methionine and 0.15 % of $CaCO_3$, and the medium is sterilized and cooled in the routine manner. This fermentation medium is aseptically inoculated with the inoculum culture prepared above and incubated at 28°C under sparging and agitation (aerated at 30.000 parts by volume/min., agitated at 250 r.p.m.). After 190 hour cultivation time, the fermentation broth is withdrawn and filtered to remove the solid matter. The resultant filtrate (26,000 parts by volume) is assayed for CPC. The titer of CPC is found to be 9,500 $\mu$g/ml. Thereafter, the procedure of Example 1 is followed to obtain 165 parts by weight of CPC sodium dihydrate.

What we claim is:

1. A method for producing cephalosporin c, which comprises cultivating a cephalosporin C-producing, polyene-antibiotics-resistant mold belonging to the genus Cephalosporium in a culture medium containing an assimilable carbon source and a digestible nitrogen source to accumulate cephalosporin C in said medium, and recovering the accumulated cephalosporin C from the medium, said mold being induced from a parent microorganism and having an increased resistance to polyene-antibiotics of not less than 20 percent over the corresponding resistance of the parent microorganism.

2. A method according to claim 1, wherein said mold belongs to *Cephalosporium acremonium*.

3. A method according to claim 1, wherein said mold belongs to *Cephalosporium polyaleurum*.

4. A method according to claim 1, wherein said mold is *Cephalosporium acremonium* K-121 (FERM-P No.

2285, IFO-9998, ATCC-20427).

5. A method according to claim 1, wherein said mold is *Cephalosporium acremonium* N-75 (FERM-P No. 2286, IFO-9997, ATCC-20428).

\* \* \* \* \*